US012688936B2

(12) United States Patent
Farnan et al.

(10) Patent No.: US 12,688,936 B2
(45) Date of Patent: Jul. 21, 2026

(54) SYSTEM AND METHOD OF PAIRING AN INFUSION PUMP WITH A REMOTE CONTROL DEVICE

(71) Applicant: Tandem Diabetes Care, Inc., San Diego, CA (US)

(72) Inventors: Jason Farnan, San Diego, CA (US); Zion Greenlee, San Diego, CA (US); Geoffrey A. Kruse, San Diego, CA (US); Michael Michaud, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 18/636,440

(22) Filed: Apr. 16, 2024

(65) Prior Publication Data

US 2024/0257966 A1 Aug. 1, 2024

Related U.S. Application Data

(63) Continuation of application No. 17/962,652, filed on Oct. 10, 2022, now Pat. No. 11,984,223, which is a
(Continued)

(51) Int. Cl.
G16H 20/17 (2018.01)
A61M 5/142 (2006.01)
(Continued)

(52) U.S. Cl.
CPC ........ G16H 40/67 (2018.01); A61M 5/14248 (2013.01); G16H 20/17 (2018.01);
(Continued)

(58) Field of Classification Search
CPC ......... G16H 40/67; G16H 20/17; H02J 50/10; H02J 50/80; H04W 76/14;
(Continued)

(56) References Cited

U.S. PATENT DOCUMENTS

RE28,890 E 7/1976 Ingram et al.
4,624,661 A 11/1986 Arimond
(Continued)

FOREIGN PATENT DOCUMENTS

EP 2624 7 45 A2 8/2013
WO 2005018507 A2 3/2005
(Continued)

OTHER PUBLICATIONS

Application and File history for U.S. Appl. No. 16/507,146, filed Jul. 10, 2019, Inventors Farnan et al.
(Continued)

*Primary Examiner* — April G Gonzales
(74) *Attorney, Agent, or Firm* — Straylight LLP

(57) ABSTRACT

Embodiments of the present disclosure enable a user-wearable infusion pump that may have a limited user interface including no display to be paired with a remote control device that can include a remote consumer electronic device such as a smartphone and/or a dedicated remote controller.

20 Claims, 14 Drawing Sheets

Related U.S. Application Data continuation of application No. 17/145,809, filed on Jan. 11, 2021, now Pat. No. 11,464,901, which is a continuation of application No. 16/507,146, filed on Jul. 10, 2019, now Pat. No. 10,888,655.

(60) Provisional application No. 62/807,496, filed on Feb. 19, 2019.

(51) Int. Cl.

| | |
|---|---|
| *G16H 40/67* | (2018.01) |
| *H02J 50/10* | (2016.01) |
| *H04W 76/14* | (2018.01) |
| *H02J 50/80* | (2016.01) |

(52) U.S. Cl.
CPC ............ *H02J 50/10* (2016.02); *H04W 76/14* (2018.02); *A61M 2205/18* (2013.01); *A61M 2205/3553* (2013.01); *A61M 2205/3584* (2013.01); *A61M 2205/3592* (2013.01); *A61M 2205/50* (2013.01); *A61M 2205/502* (2013.01); *A61M 2205/581* (2013.01); *A61M 2205/584* (2013.01); *A61M 2205/587* (2013.01); *A61M 2205/8206* (2013.01); *A61M 2205/8243* (2013.01); *H02J 50/80* (2016.02)

(58) Field of Classification Search
CPC .......... A61M 5/14248; A61M 2205/18; A61M 2205/3553; A61M 2205/3584; A61M 2205/3592; A61M 2205/50; A61M 2205/502; A61M 2205/584; A61M 2205/587; A61M 2205/8206; A61M 2205/8243
USPC ....................................................... 455/41.2
See application file for complete search history.

(56) References Cited

U.S. PATENT DOCUMENTS

| | | | |
|---|---|---|---|
| 4,678,460 | A | 7/1987 | Rosner |
| 5,000,739 | A | 3/1991 | Kulisz et al. |
| 5,558,638 | A | 9/1996 | Evers et al. |
| 5,578,832 | A | 11/1996 | Trulson et al. |
| 5,582,593 | A | 12/1996 | Hultman |
| 5,593,552 | A | 1/1997 | Joshi et al. |
| 5,704,366 | A | 1/1998 | Tacklind et al. |
| 5,860,957 | A | 1/1999 | Jacobsen et al. |
| 5,954,752 | A | 9/1999 | Mongeon et al. |
| 6,013,020 | A | 1/2000 | Meloul et al. |
| 6,017,318 | A | 1/2000 | Gauthier et al. |
| 6,070,761 | A | 6/2000 | Bloom et al. |
| 6,144,866 | A | 11/2000 | Miesel et al. |
| 6,165,155 | A | 12/2000 | Jacobsen et al. |
| 6,185,460 | B1 | 2/2001 | Thompson |
| 6,223,080 | B1 | 4/2001 | Thompson |
| 6,238,423 | B1 | 5/2001 | Bardy |
| 6,398,718 | B1 | 6/2002 | Yachia et al. |
| 6,402,689 | B1 | 6/2002 | Scarantino et al. |
| 6,488,652 | B1 | 12/2002 | Weijand et al. |
| 6,514,689 | B2 | 2/2003 | Han et al. |
| 6,561,978 | B1 | 5/2003 | Conn et al. |
| 6,564,104 | B2 | 5/2003 | Nelson et al. |
| 6,594,634 | B1 | 7/2003 | Hampton et al. |
| 6,610,003 | B1 | 8/2003 | Meloul et al. |
| 6,649,403 | B1 | 11/2003 | McDevitt et al. |
| 6,656,159 | B2 | 12/2003 | Flaherty |
| 6,683,690 | B1 | 1/2004 | Tobias |
| 6,740,059 | B2 | 5/2004 | Flaherty |
| 6,804,555 | B2 | 10/2004 | Warkentin |
| 6,821,249 | B2 | 11/2004 | Casscells, III et al. |
| 6,827,524 | B2 | 12/2004 | Starry, Jr. et al. |
| 6,857,572 | B2 | 2/2005 | Martin |
| 6,864,101 | B1 | 3/2005 | Winkler et al. |
| 6,916,159 | B2 | 7/2005 | Rush et al. |
| 6,943,034 | B1 | 9/2005 | Winkler et al. |
| 6,960,192 | B1 | 11/2005 | Flaherty et al. |
| 6,963,770 | B2 | 11/2005 | Scarantino et al. |
| 6,970,742 | B2 | 11/2005 | Mann et al. |
| 7,010,340 | B2 | 3/2006 | Scarantino et al. |
| 7,011,630 | B2 | 3/2006 | Desai et al. |
| 7,025,716 | B1 | 4/2006 | Meloul et al. |
| 7,029,455 | B2 | 4/2006 | Flaherty |
| 7,053,761 | B2 | 5/2006 | Schofield et al. |
| 7,070,577 | B1 | 7/2006 | Haller et al. |
| 7,089,608 | B2 | 8/2006 | Erb |
| 7,137,964 | B2 | 11/2006 | Flaherty |
| 7,144,384 | B2 | 12/2006 | Gorman et al. |
| 7,181,505 | B2 | 2/2007 | Haller et al. |
| 7,193,521 | B2 | 3/2007 | Moberg et al. |
| 7,198,603 | B2 | 4/2007 | Penner et al. |
| 7,204,823 | B2 | 4/2007 | Estes et al. |
| 7,291,107 | B2 | 11/2007 | Hellwig et al. |
| 7,303,549 | B2 | 12/2007 | Flaherty et al. |
| 7,316,899 | B2 | 1/2008 | McDevitt et al. |
| 7,366,925 | B2 | 4/2008 | Keely et al. |
| 7,385,443 | B1 | 6/2008 | Denison |
| 7,399,401 | B2 | 7/2008 | Rush |
| 7,483,743 | B2 | 1/2009 | Mann et al. |
| 7,497,827 | B2 | 3/2009 | Brister et al. |
| 7,553,281 | B2 | 6/2009 | Hellwig et al. |
| 7,558,629 | B2 | 7/2009 | Keimel et al. |
| 7,604,593 | B2 | 10/2009 | Parris et al. |
| 7,605,710 | B2 | 10/2009 | Crnkovich et al. |
| 7,615,007 | B2 | 11/2009 | Shults et al. |
| 7,625,354 | B2 | 12/2009 | Hochman |
| 7,651,489 | B2 | 1/2010 | Estes et al. |
| 7,651,868 | B2 | 1/2010 | McDevitt et al. |
| 7,654,976 | B2 | 2/2010 | Peterson et al. |
| 7,654,982 | B2 | 2/2010 | Carlisle et al. |
| 7,691,330 | B1 | 4/2010 | Winkler et al. |
| 7,699,775 | B2 | 4/2010 | Desai et al. |
| 7,704,227 | B2 | 4/2010 | Moberg et al. |
| 7,711,402 | B2 | 5/2010 | Shults et al. |
| 7,713,574 | B2 | 5/2010 | Brister et al. |
| 7,714,757 | B2 | 5/2010 | Denison et al. |
| 7,722,536 | B2 | 5/2010 | Goodnow |
| 7,737,581 | B2 | 6/2010 | Spurlin et al. |
| 7,774,145 | B2 | 8/2010 | Brauker et al. |
| 7,775,975 | B2 | 8/2010 | Brister et al. |
| 7,788,369 | B2 | 8/2010 | McAllen et al. |
| 7,811,279 | B2 | 10/2010 | John |
| 7,826,382 | B2 | 11/2010 | Sicurello et al. |
| 7,837,647 | B2 | 11/2010 | Estes et al. |
| 7,850,674 | B2 | 12/2010 | Goodnow et al. |
| 7,928,850 | B2 | 4/2011 | Hayter et al. |
| 7,933,780 | B2 | 4/2011 | De La Huerga |
| 7,949,382 | B2 | 5/2011 | Jina |
| 7,973,667 | B2 | 7/2011 | Crnkovich et al. |
| 8,005,547 | B2 | 8/2011 | Forsberg et al. |
| 8,012,119 | B2 * | 9/2011 | Estes .................... A61M 5/172 604/65 |
| 8,029,443 | B2 | 10/2011 | Goodnow |
| 8,034,019 | B2 | 10/2011 | Nair et al. |
| 8,083,718 | B2 | 12/2011 | Rush et al. |
| 8,095,197 | B2 | 1/2012 | Santini, Jr. et al. |
| 8,100,852 | B2 | 1/2012 | Moberg et al. |
| 8,106,534 | B2 | 1/2012 | Spurlin et al. |
| 8,118,770 | B2 | 2/2012 | Galley et al. |
| 8,121,857 | B2 | 2/2012 | Galasso et al. |
| 8,147,511 | B2 | 4/2012 | Perry et al. |
| 8,149,117 | B2 | 4/2012 | Fennell et al. |
| 8,226,558 | B2 | 7/2012 | Say et al. |
| 8,234,128 | B2 | 7/2012 | Martucci et al. |
| 8,275,438 | B2 | 9/2012 | Simpson et al. |
| 8,277,416 | B2 | 10/2012 | Gibbs et al. |
| 8,280,476 | B2 | 10/2012 | Jina |
| 8,287,454 | B2 | 10/2012 | Wolpert et al. |
| 8,287,495 | B2 | 10/2012 | Michaud et al. |
| 8,311,749 | B2 | 11/2012 | Brauker et al. |
| 8,323,188 | B2 | 12/2012 | Tran |
| 8,357,091 | B2 | 1/2013 | Say et al. |
| 8,369,919 | B2 | 2/2013 | Kamath et al. |

(56) References Cited

U.S. PATENT DOCUMENTS

| | | |
|---|---|---|
| 8,372,351 B2 | 2/2013 | Ow-Wing |
| 8,401,194 B2 | 3/2013 | Nierzwick et al. |
| 8,402,145 B2 | 3/2013 | Holden et al. |
| 8,414,523 B2 | 4/2013 | Blomquist et al. |
| 8,414,563 B2 | 4/2013 | Kamen et al. |
| 8,444,595 B2 | 5/2013 | Brukalo et al. |
| 8,449,523 B2 | 5/2013 | Brukalo et al. |
| 8,451,230 B2 | 5/2013 | Celentano et al. |
| 8,454,554 B2 | 6/2013 | Reinke |
| 8,454,557 B1 | 6/2013 | Qi et al. |
| 8,456,301 B2 | 6/2013 | Fennell |
| 8,460,243 B2 | 6/2013 | Goodnow et al. |
| 8,461,985 B2 | 6/2013 | Fennell et al. |
| 8,502,662 B2 | 8/2013 | Pohlman et al. |
| 8,533,475 B2 | 9/2013 | Frikart et al. |
| 8,573,027 B2 | 11/2013 | Rosinko et al. |
| 8,639,288 B1 | 1/2014 | Friedman |
| 8,726,266 B2 | 5/2014 | Kiaie et al. |
| 8,932,250 B2 | 1/2015 | Montgomery et al. |
| 8,986,253 B2 | 3/2015 | DiPerna |
| 9,008,803 B2 * | 4/2015 | Blomquist ............ A61M 5/142 |
| | | 700/282 |
| 9,049,982 B2 | 6/2015 | Brukalo et al. |
| 9,132,227 B2 | 9/2015 | Bryant, Jr. et al. |
| 9,155,900 B2 | 10/2015 | Meskens |
| 9,173,992 B2 | 11/2015 | Bengtsson et al. |
| 9,381,297 B2 | 7/2016 | Brown et al. |
| 9,474,856 B2 | 10/2016 | Blomquist |
| 9,486,571 B2 | 11/2016 | Rosinko |
| 9,492,608 B2 | 11/2016 | Saint |
| 9,565,718 B2 | 2/2017 | Swanson |
| 9,603,995 B2 | 3/2017 | Rosinko et al. |
| 9,675,756 B2 | 6/2017 | Kamen et al. |
| 9,737,656 B2 | 8/2017 | Rosinko |
| 9,750,873 B2 | 9/2017 | Brown et al. |
| 9,940,441 B2 | 4/2018 | Walsh |
| 9,970,044 B2 | 5/2018 | Tonks |
| 9,970,893 B2 | 5/2018 | Morgan |
| 9,974,903 B1 | 5/2018 | Davis et al. |
| 9,980,140 B1 | 5/2018 | Spencer et al. |
| 9,993,595 B2 * | 6/2018 | Michaud ........... A61M 5/14244 |
| 10,016,561 B2 | 7/2018 | Saint et al. |
| 10,049,768 B2 | 8/2018 | Blomquist |
| 10,201,656 B2 | 2/2019 | Rosinko |
| 10,213,547 B2 | 2/2019 | Rosinko |
| 10,279,105 B2 | 5/2019 | Rosinko |
| 10,279,106 B1 * | 5/2019 | Cook ................ A61M 5/14248 |
| 10,279,107 B2 * | 5/2019 | Michaud ........... A61M 5/14248 |
| 10,357,603 B2 * | 7/2019 | Michaud ........... A61M 5/14248 |
| 10,357,607 B2 | 7/2019 | Blomquist et al. |
| 10,430,043 B2 | 10/2019 | Rosinko et al. |
| 10,463,786 B2 | 11/2019 | Saint |
| 10,478,551 B2 | 11/2019 | Rosinko |
| 10,492,141 B2 * | 11/2019 | Kruse ............... H04W 52/0232 |
| 10,736,037 B2 | 8/2020 | Kruse et al. |
| 10,773,015 B2 | 9/2020 | Blomquist et al. |
| 10,780,215 B2 | 9/2020 | Rosinko et al. |
| 10,806,851 B2 | 10/2020 | Rosinko |
| 10,864,318 B2 | 12/2020 | Michaud |
| 10,888,655 B2 | 1/2021 | Farnan et al. |
| 10,918,785 B2 | 2/2021 | Rosinko |
| 10,926,025 B2 | 2/2021 | Betts et al. |
| 11,305,057 B2 * | 4/2022 | Michaud ................ G16H 20/17 |
| 11,464,908 B2 * | 10/2022 | Michaud ............ A61M 5/1723 |
| 2001/0027791 A1 | 10/2001 | Wallace et al. |
| 2002/0040208 A1 | 4/2002 | Flaherty et al. |
| 2002/0072733 A1 | 6/2002 | Flaherty |
| 2002/0126036 A1 | 9/2002 | Flaherty et al. |
| 2003/0036683 A1 | 2/2003 | Kehr et al. |
| 2003/0060765 A1 | 3/2003 | Campbell et al. |
| 2003/0114836 A1 | 6/2003 | Estes et al. |
| 2004/0010207 A1 | 1/2004 | Flaherty et al. |
| 2004/0073161 A1 | 4/2004 | Tachibana |
| 2004/0172222 A1 | 9/2004 | Simpson et al. |
| 2004/0260233 A1 | 12/2004 | Garibotto et al. |

| | | |
|---|---|---|
| 2005/0060030 A1 | 3/2005 | Lashinski et al. |
| 2005/0085760 A1 | 4/2005 | Ware et al. |
| 2005/0137530 A1 | 6/2005 | Campbell et al. |
| 2005/0171512 A1 | 8/2005 | Flaherty |
| 2005/0228234 A1 | 10/2005 | Yang |
| 2005/0277912 A1 | 12/2005 | John |
| 2006/0001538 A1 | 1/2006 | Kraft et al. |
| 2006/0137695 A1 | 6/2006 | Hellwig et al. |
| 2006/0173444 A1 | 8/2006 | Choy et al. |
| 2007/0150019 A1 | 6/2007 | Youker et al. |
| 2007/0233051 A1 | 10/2007 | Hohl et al. |
| 2007/0287985 A1 | 12/2007 | Estes et al. |
| 2008/0004601 A1 | 1/2008 | Jennewine et al. |
| 2008/0017194 A1 | 1/2008 | Hassanein et al. |
| 2008/0089313 A1 | 4/2008 | Cayo et al. |
| 2008/0097912 A1 | 4/2008 | Dicks et al. |
| 2008/0097913 A1 | 4/2008 | Dicks et al. |
| 2008/0097914 A1 | 4/2008 | Dicks et al. |
| 2008/0097917 A1 | 4/2008 | Dicks et al. |
| 2008/0125700 A1 | 5/2008 | Moberg et al. |
| 2008/0125701 A1 | 5/2008 | Moberg et al. |
| 2008/0195060 A1 | 8/2008 | Roger et al. |
| 2008/0208627 A1 | 8/2008 | Skyggebjerg |
| 2008/0215035 A1 | 9/2008 | Yodfat et al. |
| 2008/0215120 A1 | 9/2008 | Dicks et al. |
| 2008/0224852 A1 | 9/2008 | Dicks et al. |
| 2008/0231226 A1 | 9/2008 | Hoffman et al. |
| 2008/0287922 A1 * | 11/2008 | Panduro ................. G16H 20/17 |
| | | 604/890.1 |
| 2008/0294024 A1 | 11/2008 | Cosentino et al. |
| 2008/0312584 A1 | 12/2008 | Montgomery et al. |
| 2009/0037020 A1 | 2/2009 | Brown |
| 2009/0069868 A1 | 3/2009 | Bengtsson et al. |
| 2009/0085768 A1 | 4/2009 | Patel et al. |
| 2009/0088731 A1 | 4/2009 | Campbell et al. |
| 2009/0108016 A1 | 4/2009 | Brown et al. |
| 2009/0115628 A1 | 5/2009 | Dicks et al. |
| 2009/0177142 A1 * | 7/2009 | Blomquist .......... A61M 5/1413 |
| | | 715/716 |
| 2009/0192366 A1 | 7/2009 | Mensinger et al. |
| 2009/0192724 A1 | 7/2009 | Brauker et al. |
| 2009/0192745 A1 | 7/2009 | Kamath et al. |
| 2009/0209945 A1 | 8/2009 | Lobl et al. |
| 2009/0212966 A1 * | 8/2009 | Panduro ................. G16H 40/63 |
| | | 340/4.31 |
| 2009/0227855 A1 | 9/2009 | Hill et al. |
| 2009/0227888 A1 | 9/2009 | Salmi et al. |
| 2009/0240193 A1 | 9/2009 | Mensinger et al. |
| 2009/0254037 A1 | 10/2009 | Bryant, Jr. et al. |
| 2009/0267774 A1 | 10/2009 | Enegren et al. |
| 2009/0267775 A1 | 10/2009 | Enegren et al. |
| 2009/0270705 A1 | 10/2009 | Enegren et al. |
| 2009/0281393 A1 | 11/2009 | Smith |
| 2009/0306594 A1 * | 12/2009 | Pang ................. A61M 5/14276 |
| | | 307/66 |
| 2010/0022937 A1 | 1/2010 | Bedingfield et al. |
| 2010/0023582 A1 | 1/2010 | Pedersen et al. |
| 2010/0063765 A1 | 3/2010 | Carlisle |
| 2010/0093319 A1 | 4/2010 | Sherman |
| 2010/0094110 A1 | 4/2010 | Heller et al. |
| 2010/0121169 A1 | 5/2010 | Petisce et al. |
| 2010/0134305 A1 | 6/2010 | Lu et al. |
| 2010/0152811 A1 | 6/2010 | Flaherty |
| 2010/0160759 A1 | 6/2010 | Celentano et al. |
| 2010/0179402 A1 | 7/2010 | Goode, Jr. et al. |
| 2010/0192686 A1 | 8/2010 | Kamen et al. |
| 2010/0198142 A1 | 8/2010 | Sloan et al. |
| 2010/0198183 A1 | 8/2010 | Lanigan et al. |
| 2010/0211011 A1 * | 8/2010 | Haar ................. A61M 5/14248 |
| | | 604/151 |
| 2010/0234709 A1 | 9/2010 | Say et al. |
| 2010/0235439 A1 | 9/2010 | Goodnow |
| 2010/0274218 A1 | 10/2010 | Yodfat et al. |
| 2010/0286653 A1 | 11/2010 | Kubel et al. |
| 2010/0292556 A1 | 11/2010 | Golden |
| 2010/0305421 A1 | 12/2010 | Ow-Wing |
| 2010/0324382 A1 | 12/2010 | Cantwell et al. |
| 2011/0009824 A1 | 1/2011 | Yodfat et al. |
| 2011/0040247 A1 | 2/2011 | Mandro et al. |

(56) References Cited

U.S. PATENT DOCUMENTS

| | | | |
|---|---|---|---|
| 2011/0040251 A1* | 2/2011 | Blomquist | A61M 5/1413 604/151 |
| 2011/0044333 A1 | 2/2011 | Sicurello et al. | |
| 2011/0046469 A1 | 2/2011 | Nelson et al. | |
| 2011/0047499 A1 | 2/2011 | Mandro et al. | |
| 2011/0066555 A1 | 3/2011 | Dicks et al. | |
| 2011/0078441 A1 | 3/2011 | Dicks et al. | |
| 2011/0149759 A1 | 6/2011 | Jollot | |
| 2011/0152770 A1 | 6/2011 | DiPerna et al. | |
| 2011/0152970 A1 | 6/2011 | Jollot et al. | |
| 2011/0169610 A1 | 7/2011 | Geissler et al. | |
| 2011/0172744 A1 | 7/2011 | Davis et al. | |
| 2011/0190614 A1 | 8/2011 | Brister et al. | |
| 2011/0190694 A1 | 8/2011 | Lanier, Jr. et al. | |
| 2011/0193704 A1 | 8/2011 | Harper et al. | |
| 2011/0201911 A1 | 8/2011 | Johnson et al. | |
| 2011/0213329 A1 | 9/2011 | Yodfat et al. | |
| 2011/0213621 A1 | 9/2011 | Dicks et al. | |
| 2011/0256024 A1 | 10/2011 | Cole et al. | |
| 2011/0257895 A1 | 10/2011 | Brauker et al. | |
| 2012/0022324 A1 | 1/2012 | Forsell | |
| 2012/0029433 A1* | 2/2012 | Michaud | A61M 5/1413 604/151 |
| 2012/0041415 A1 | 2/2012 | Estes et al. | |
| 2012/0091813 A1* | 4/2012 | Spurlin | G06F 1/30 307/66 |
| 2012/0095393 A1* | 4/2012 | Reinke | G16H 20/17 604/66 |
| 2012/0116197 A1 | 5/2012 | Moberg et al. | |
| 2012/0185267 A1* | 7/2012 | Kamen | A61B 5/0024 705/2 |
| 2012/0232520 A1* | 9/2012 | Sloan | A61B 5/14532 604/504 |
| 2012/0277667 A1* | 11/2012 | Yodat | A61B 5/1451 604/65 |
| 2012/0302991 A1 | 11/2012 | Blomquist et al. | |
| 2013/0042865 A1 | 2/2013 | Monsees | |
| 2013/0053816 A1* | 2/2013 | DiPerna | A61M 5/1408 604/151 |
| 2013/0162426 A1 | 6/2013 | Wiesner et al. | |
| 2013/0283196 A1 | 10/2013 | Farnan et al. | |
| 2013/0317837 A1 | 11/2013 | Ballantyme | |
| 2013/0324928 A1* | 12/2013 | Kruse | A61M 5/16854 604/151 |
| 2013/0331790 A1* | 12/2013 | Brown | H01R 13/5224 604/151 |
| 2014/0054883 A1 | 2/2014 | Lanigan et al. | |
| 2014/0075169 A1 | 3/2014 | Andrews | |
| 2014/0113553 A1 | 4/2014 | Brukalo et al. | |
| 2014/0175682 A1* | 6/2014 | Johnson | A61L 9/127 261/30 |
| 2014/0187890 A1 | 7/2014 | Mensinger et al. | |
| 2014/0200426 A1 | 7/2014 | Taub et al. | |
| 2014/0276419 A1 | 9/2014 | Rosinko et al. | |
| 2014/0276423 A1* | 9/2014 | Lecanu-Fayet | A61M 5/162 604/262 |
| 2014/0323961 A1 | 10/2014 | Blomquist et al. | |
| 2014/0371816 A1 | 12/2014 | Matos | |
| 2015/0011970 A1 | 1/2015 | Kamen et al. | |
| 2015/0052511 A1 | 2/2015 | Kiaie et al. | |
| 2015/0077038 A1 | 3/2015 | Chao et al. | |
| 2015/0174320 A1 | 6/2015 | Grant et al. | |
| 2015/0187187 A1* | 7/2015 | Del Toro | H04W 68/005 340/539.11 |
| 2015/0314062 A1 | 11/2015 | Blomquist et al. | |
| 2016/0004390 A1 | 1/2016 | Laska | |
| 2016/0015888 A1 | 1/2016 | Tieck et al. | |
| 2016/0074573 A1* | 3/2016 | Kohlbrecher | G16H 20/17 604/151 |
| 2016/0098848 A1 | 4/2016 | Zamanakos et al. | |
| 2016/0228041 A1 | 8/2016 | Heller et al. | |
| 2016/0267242 A1* | 9/2016 | Naker | G16H 40/67 |
| 2016/0271325 A1 | 9/2016 | Farnan et al. | |
| 2016/0328991 A1 | 11/2016 | Simpson et al. | |
| 2016/0339172 A1* | 11/2016 | Michaud | A61M 5/14244 |
| 2016/0367753 A1* | 12/2016 | Kamen | A61M 5/14248 |
| 2017/0049957 A1* | 2/2017 | Michaud | A61M 5/14248 |
| 2017/0049960 A1 | 2/2017 | Nguyen | |
| 2017/0056590 A1 | 3/2017 | DiPerna et al. | |
| 2017/0127462 A1* | 5/2017 | Liu | H04W 76/28 |
| 2017/0142658 A1* | 5/2017 | Kruse | H04W 4/02 |
| 2017/0173261 A1* | 6/2017 | O'Connor | A61M 5/14248 |
| 2017/0179749 A1 | 6/2017 | Mansour | |
| 2017/0216523 A1* | 8/2017 | Neftel | A61M 5/172 |
| 2017/0266381 A1* | 9/2017 | Bryant, Jr. | A61M 5/1723 |
| 2017/0290535 A1* | 10/2017 | Rao | A61B 5/14532 |
| 2017/0300206 A1 | 10/2017 | Rosinko et al. | |
| 2017/0312423 A1 | 11/2017 | Rosinko | |
| 2018/0071454 A1* | 3/2018 | Betts | B65B 3/003 |
| 2018/0193555 A1* | 7/2018 | Michaud | A61M 5/14248 |
| 2018/0204636 A1* | 7/2018 | Edwards | G16H 40/67 |
| 2020/0101224 A1 | 4/2020 | Lintereur | |
| 2022/0031456 A1* | 2/2022 | Navia | A61F 2/2454 |
| 2023/0030704 A1* | 2/2023 | Weinstein | A61C 7/14 |
| 2023/0043768 A1* | 2/2023 | Abraham | E21B 47/26 |
| 2024/0370839 A1* | 11/2024 | Sharpe | G06N 20/00 |

FOREIGN PATENT DOCUMENTS

| | | | |
|---|---|---|---|
| WO | 2007098265 A2 | 8/2007 | |
| WO | 2007098287 A2 | 8/2007 | |
| WO | 2009013736 A1 | 1/2009 | |
| WO | 2009016636 A2 | 2/2009 | |
| WO | 2016059616 A1 | 4/2016 | |
| WO | 2016145094 A2 | 9/2016 | |
| WO | 2017007775 A2 | 1/2017 | |
| WO | 2018111928 A1 | 6/2018 | |

OTHER PUBLICATIONS

Application and File history for U.S. Appl. No. 15/868,461, filed Jan. 11, 2018, Inventors Michaud et al.

Application and File history for U.S. Appl. No. 16/502,196, filed Jul. 3, 2019, Inventors Michaud et al.

Application and File history for U.S. Appl. No. 16/830,415, filed Mar. 26, 2020, Inventors Michaud et al.

International Search Report and Written Opinion for PCT Application No. PCT/US2019/041096, mailed on Nov. 15, 2019, 11 pages.

Wu J., et al., "Wireless Power and Data Transfer via a Common Inductive Link Using Frequency Division Multiplexing," IEEE Transactions on Industrial Electronics, vol. 62 (12), Jul. 9, 2015, pp. 1-10.

Sony Corporation, MDR-ZX880BN Help Guide, 2016 SONY https://helpguide.sony.neet/rndr/zx770bn/v1/en/contents/TP0000773472.html (Year: 2016).

Application and File history for U.S. Appl. No. 17/145,809, filed Jan. 11, 2021. Inventors Farnan.

Extended European Search Report for Application No. , dated Oct. 10, 2022, 8 pages.

International Preliminary Report on Patentability for Application No. PCT/US2018/013331, mailed on Jul. 25, 2019, 6 pages.

International Search Report and Written Opinion for Application No. PCT/US2018/013331, mailed on May 3, 2018, 12 pages.

Search Report and Written Opinion mailed Jul. 25, 2020 for PCT Application No. PCT/US2020/024857, 11 pages.

Search Report dated Jun. 29, 2020 for EP Application No. 187390329.8, 8 pages.

* cited by examiner

171

171

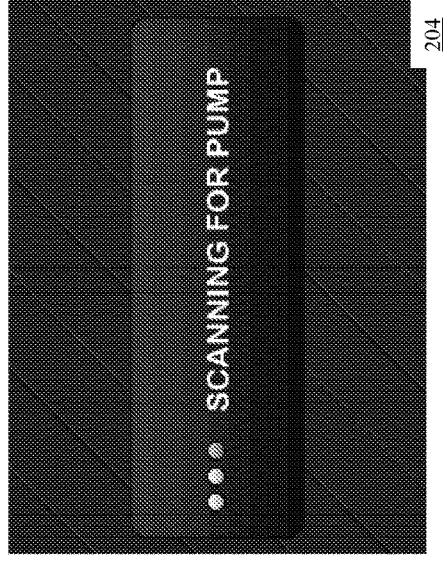
*Fig. 7B*
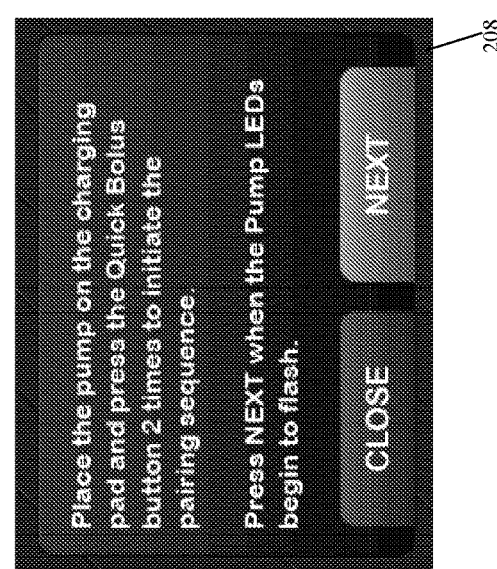
*Fig. 7D*
*Fig. 7A*
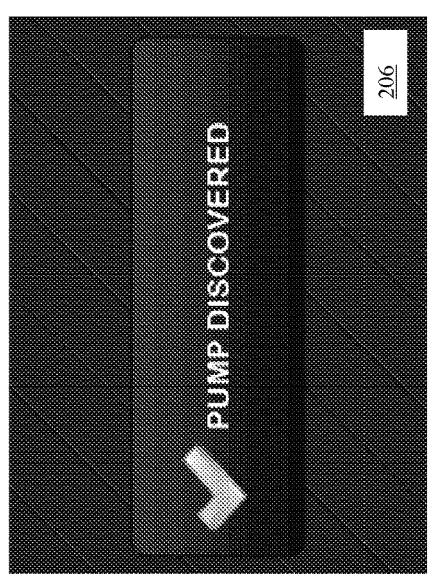
*Fig. 7C*

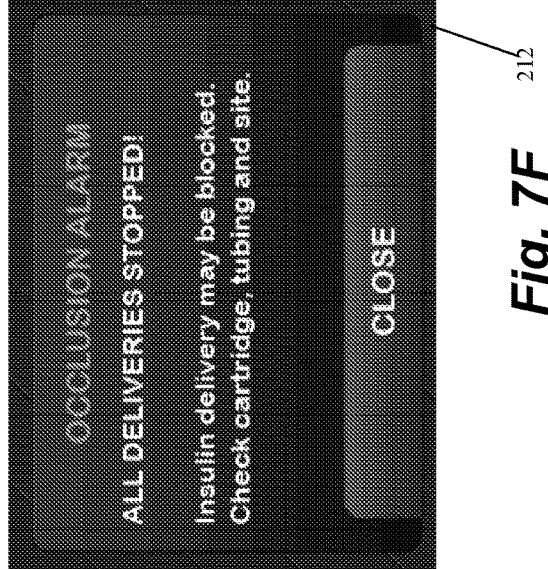

OCCLUSION ALARM

ALL DELIVERIES STOPPED!

Insulin delivery may be blocked.
Check cartridge, tubing and site.

CLOSE

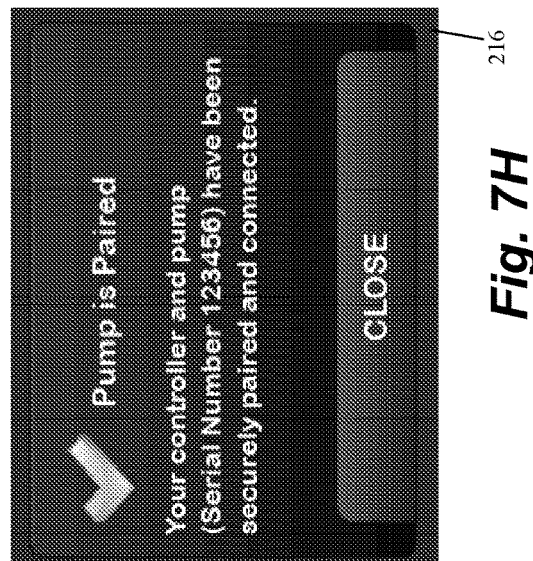

Pump is Paired

Your controller and pump
(Serial Number 123456) have been
securely paired and connected.

CLOSE

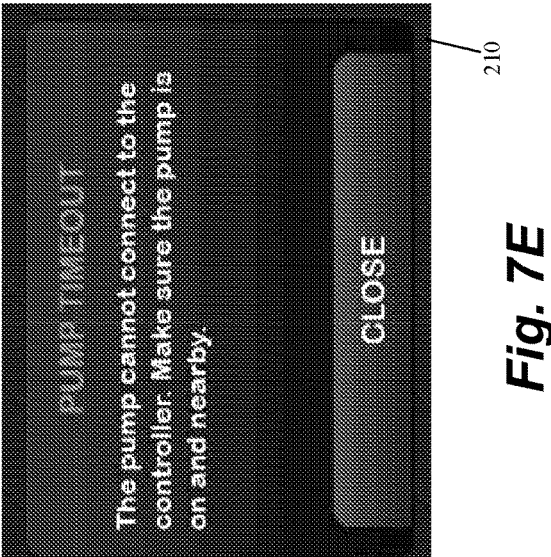

PUMP TIMEOUT

The pump cannot connect to the
controller. Make sure the pump is
on and nearby.

CLOSE

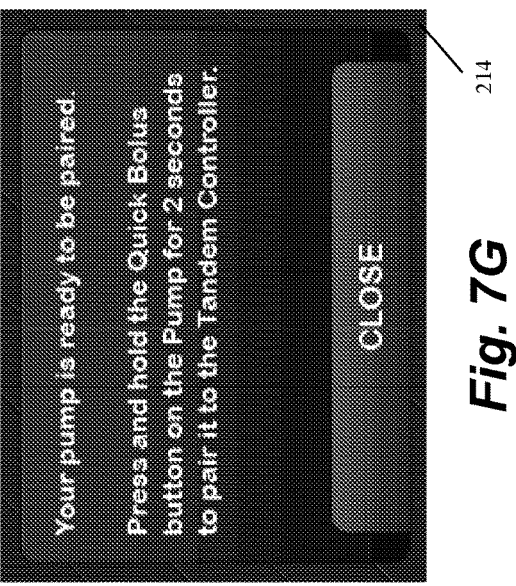

Your pump is ready to be paired.

Press and hold the Quick Bolus
button on the Pump for 2 seconds
to pair it to the Tandem Controller.

CLOSE

SYSTEM AND METHOD OF PAIRING AN INFUSION PUMP WITH A REMOTE CONTROL DEVICE

RELATED APPLICATIONS

This application is a continuation of U.S. patent application Ser. No. 17/962,652, filed Oct. 10, 2022, which is a continuation of U.S. patent application Ser. No. 17/145,809, filed Jan. 11, 2021, now U.S. Pat. No. 11,464,901, which in turn in a continuation of U.S. patent application Ser. No. 16/507,146, filed Jul. 10, 2019, now U.S. Pat. No. 10,888, 655, issued Jan. 12, 2021, which claims benefit of U.S. Provisional Application No. 62/807,496, filed Feb. 19, 2019, each of which is hereby incorporated herein in its entirety by reference.

TECHNICAL FIELD

The present invention relates to medical pumps for delivering medicament to a patient, and more specifically, to a user-wearable pump controllable with a remote control device.

BACKGROUND

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of insulin injecting pumps that have been developed for the administration of insulin for those suffering from both Type 1 and Type 2 diabetes. Some insulin injecting pumps configured as portable infusion devices can provide continuous subcutaneous insulin injection and/or infusion therapy for the treatment of diabetes. Therapy may include the regular and/or continuous injection or infusion of insulin into the skin of a person suffering from diabetes and offer an alternative to multiple daily injections of insulin by an insulin syringe or an insulin pen. These pumps can be ambulatory/portable infusion pumps that are worn by the user and may use replaceable cartridges. Medicaments other than or in addition to insulin, such as glucagon, pramlintide, etc. can also be delivered. Examples of such pumps and various features that can be associated with such pumps include those disclosed in U.S. Patent Application Publication No. 2013/0053816, U.S. Pat. Nos. 8,573,027, 8,986, 253, U.S. Patent Application Publication No. 2013/0324928, U.S. Patent Application Publication No. 2013/0331790, U.S. Pat. No. 8,287,495 and U.S. patent application Ser. No. 15/158,125, each of which is hereby incorporated herein by reference in its entirety.

One type of pump that has been developed is a patch pump, or micro pump. Patch pumps are small pumps, typically ambulatory, that may be carried directly on the skin under the user's clothing. In some cases, the pumps are situated directly on, or very near to, the injection site such that little or no tubing is required to deliver the insulin or other medicament to the patient. Some patch pumps include a single button on the pump to initiate delivery of medicament and do not include a built-in display or user interface.

These pumps are therefore primarily remote-controlled. Having only a single button on the pump provides the advantage of being more robust for waterproofing and resistance to external contaminants. However, a disadvantage is that the functionality of a pump with a single button is limited without the use of a remote control apparatus, typically including a user interface.

With the proliferation of handheld electronic devices, such as mobile phones (e.g., smartphones), there is a desire to be able to remotely utilize such devices, as well as dedicated wireless controllers designed to work with one or more infusion pumps and/or types of infusion pumps, to optimize usage of infusion pumps. These remote controllers would enable a pump to be monitored, programmed and/or operated more privately, more conveniently and more comfortably. Accordingly, one potential use of dedicated remote devices and handheld consumer electronic devices (such as smartphones, tablets and the like) is to utilize such devices as controllers for remotely programming and/or operating infusion pumps.

To use a smartphone or dedicated remote control device to control an infusion pump, the device must be paired with the particular pump in order to enable the pump to execute commands sent by the remote device. However, with patch pumps described above that may not have a display or robust user interface, there is a limited ability to enter input into the pump to pair the pump with the remote and/or to provide an indication from the pump that the pump has been paired.

SUMMARY

Embodiments of the present disclosure enable a user-wearable infusion pump that may have a limited user interface including no display to be paired with a remote control device that can include a remote consumer electronic device such as a smartphone and/or a dedicated remote controller.

In embodiments, a user-wearable infusion pump includes one or more indicator lights, a single input button and no visual display. Such a pump can be paired for wireless control with a remote control device by following a step by step sequence of instructions displayed on the display of the remote control device. The sequence can include instructions for how to position the pump during the pairing process, such as on an inductive charging pad. The sequence can further include instructions to the user to interact with the input button on the pump in particular ways at particular stages of the pairing process. Feedback to the user as to whether or not the pairing process is being properly navigated and completed can be provided by the one or more indicator lights of the pump as well as on the display of the remote control device during the sequence of instructions.

In an embodiment, a method of pairing a user-wearable infusion pump including one or more indicator lights and no display screen with a remote control device is provided. The method includes receiving input at the remote control device to initiate a pairing procedure for pairing the remote control device with the user-wearable infusion pump and determining, with the remote control device, whether the user-wearable infusion pump is available for the pairing procedure. After determining that the user-wearable infusion pump is available for the pairing procedure, the remote control device can initiate the pairing procedure. Step by step instructions for the pairing procedure can be presented on a display screen of the remote control device and visual feedback as to an ongoing status of the pairing procedure can be provided with the one or more indicator lights of the user-wearable infusion pump. Successful pairing of the remote control device with the user-wearable infusion pump can be confirmed with both the display screen of the remote control device and the one or more indicator lights of the user-wearable infusion pump.

In an embodiment, a system for pairing an infusion pump with a remote control device can include a user-wearable infusion pump including one or more indicator lights and no display screen and a remote control device including a display screen. The remote control device can include a processor configured to receive input at the remote control device to initiate a pairing procedure for pairing the remote control device with the user-wearable infusion pump and determine whether the user-wearable infusion pump is available for the pairing procedure. The processor can initiate the pairing procedure with the remote control device after determining that the user-wearable infusion pump is available for the pairing procedure. Step by step instructions for the pairing procedure can be presented on the display screen of the remote control device and the user-wearable infusion pump can provide visual feedback as to an ongoing status of the pairing procedure with the one or more indicator lights. Successful pairing of the remote control device with the user-wearable infusion pump can be indicated with both the display screen of the remote control device and the one or more indicator lights of the user-wearable infusion pump.

The above summary is not intended to describe each illustrated embodiment or every implementation of the subject matter hereof The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 7A-7I depict exemplary screen shots on a remote control device for the pairing sequences of FIGS. 6, 8 and/or 10.

Figures 1A, 1B, 1C:
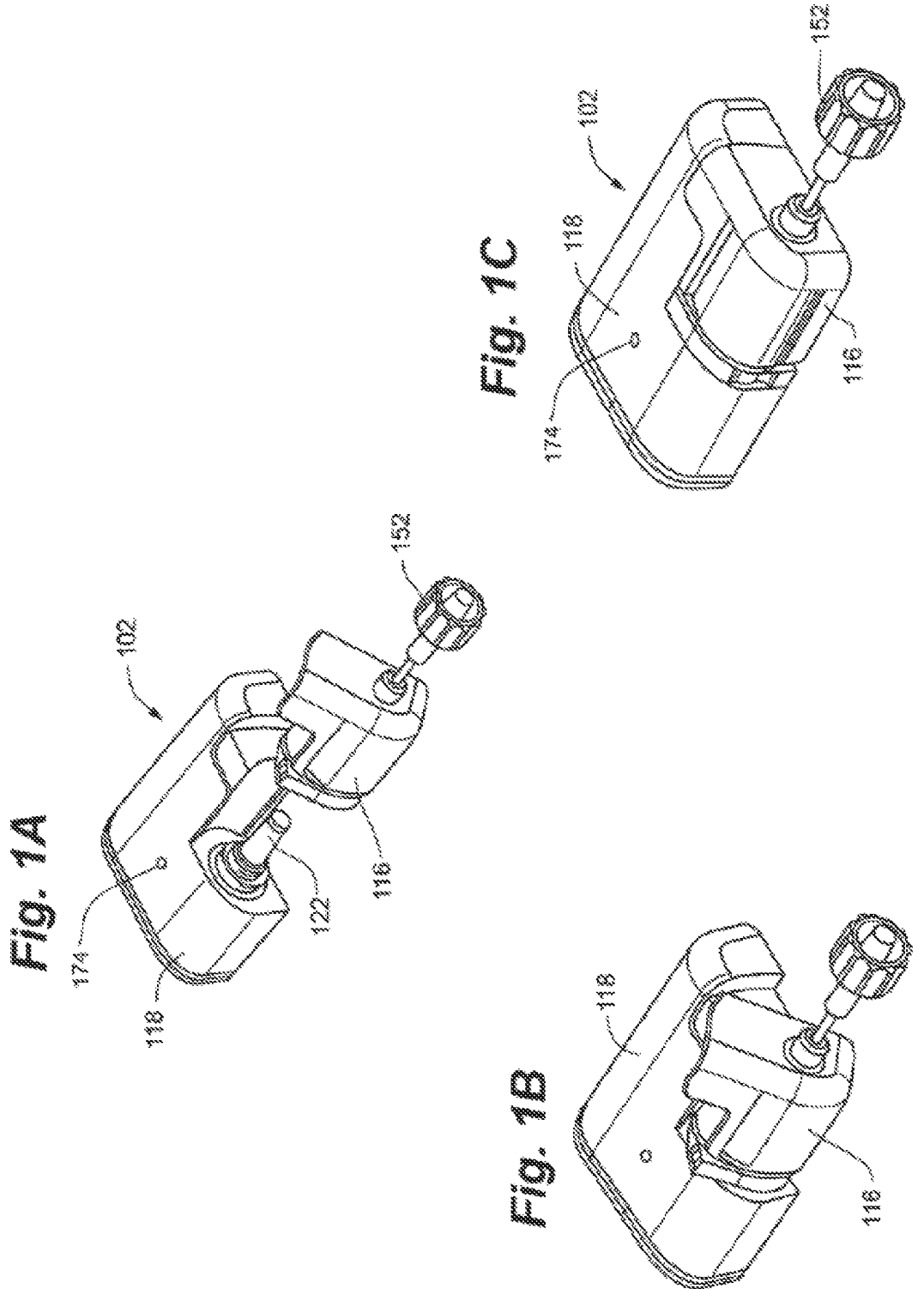
FIGS. 1A-1C depicts an embodiment of a pump system according to the disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Referring to FIGS. 1A-1C, a pump system 100 including a pump 102 is depicted in accordance with an embodiment of the disclosure. Drive unit 118 of pump 102 includes a drive mechanism 122 that mates with a recess in medicament cartridge 116 of pump 102 to attach the medicament cartridge 116 to the drive unit 118. Further details regarding example embodiments of such delivery mechanisms can be found in U.S. Patent Publication No. 2017/0049957, which is hereby incorporated by reference in its entirety.

Figures 2A, 2B:
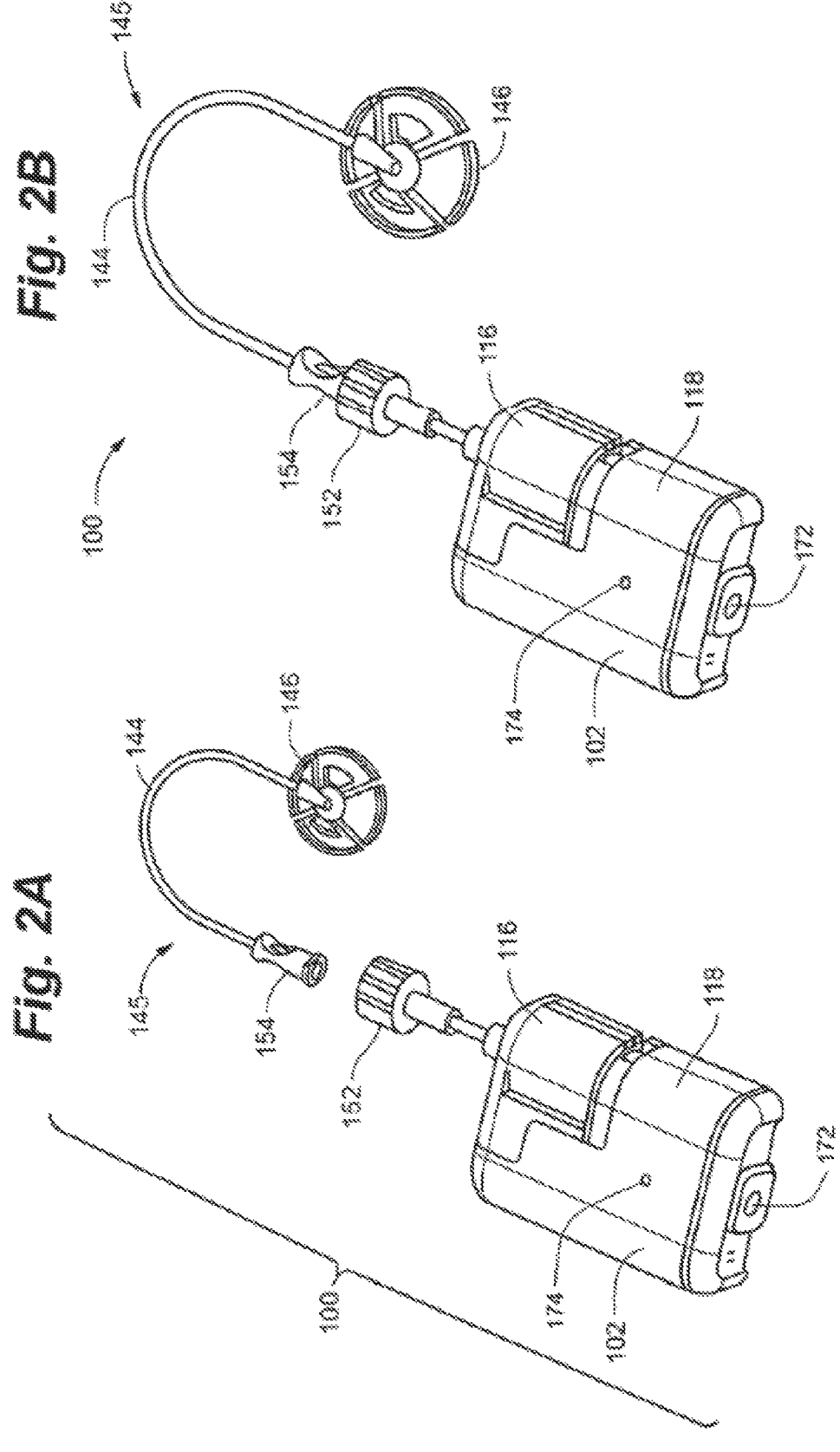
FIGS. 2A-2C depict an embodiment of a pump system according to the disclosure.

As depicted in the embodiment of FIGS. 2A-2B, pump system 100 can include a pump 102 and an infusion set 145. FIG. 2A depicts this infusion set 145 as not connected to pump while FIG. 2B depicts infusion set 145 connected to pump 102 via connectors 154 and 152. Infusion set 145 can include tubing 144 extending between a connector 154 and a site connector 146. Connector 154 can be configured to couple to pump 102 at connector 152. Site connector 146 can be configured to be attached to an infusion site on a user, while pump 102 can be carried in a separate location, such as the user's pocket or another location on the user's body. Various lengths of tubing 144 can be used in this embodiment to accommodate the user's preference. Further details regarding such pumps can be found in U.S. Pat. Nos. 9,993,595; 10,279,106; and 10,279,107, each of which is hereby incorporated herein by reference in its entirety.

In one embodiment, pump 102 includes a processor that controls operations of the pump and, in some embodiments, may communicate in either one-way or two-way modes to, e.g., receive operational commands and/or other signals, including data, from a separate device and/or, e.g., to send signals, including data, to a separate device. Pump 102 can include one or more buttons configured to cause the processor to initiate one or more functions. In the depicted embodiment, pump 102 includes only a single button 172, although more than one button may be present on pump 102. Button 172 can be configured to, for example, initiate delivery of medicament. Any single button such as button 172 can be utilized to execute a plurality of functions or operations. For example, a single press of button may initiate one function, holding the button down for a predetermined period of time may initiate another function, etc. Because the depicted pump 102 optionally does not itself include a display or user interface, information and feedback regarding medicament delivery or dosing initiated with button 172 can be communicated to and displayed on a remote control device or other device having a display and/or other type of user interface. Further details regarding use of button 172 can be found in U.S. Patent Publication No. 2018/0193555, which is hereby incorporated by reference in its entirety.

Figure 2C:
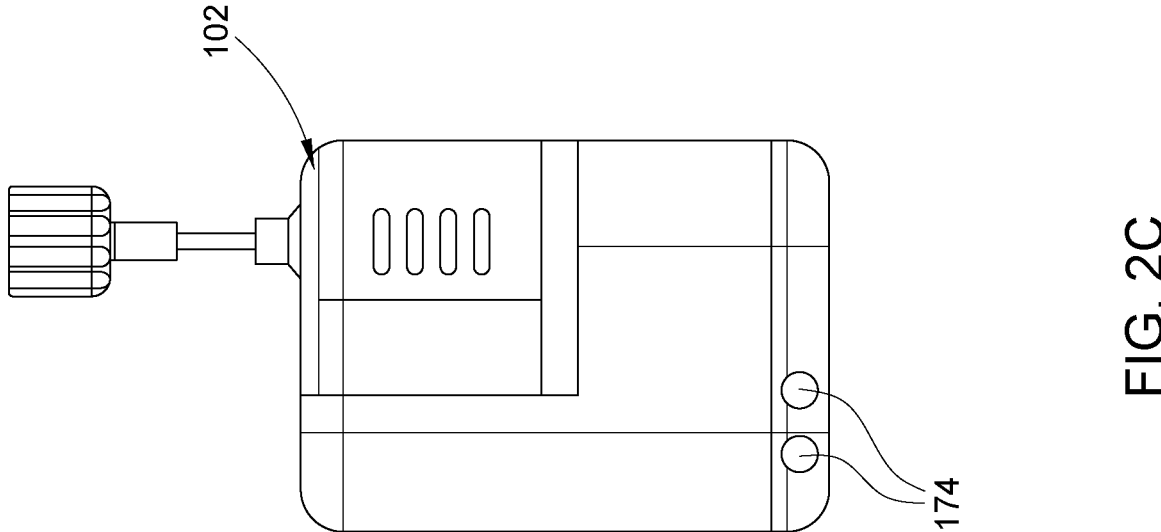

In one embodiment, pump 102 includes a light source, such as a light emitting diode (LED) 174. Light source 174 can be configured to provide user feedback regarding user input and/or the performance of a desired function. For example, in one embodiment, light source 174 can illuminate or blink one or more times to indicate that the one or more buttons 172 have been activated and/or that a desired function has been initiated. In one embodiment, pump 102 can additionally and/or alternatively vibrate and/or provide audible notifications to indicate that the one or more buttons 172 have been activated and/or that a desired function has been initiated or, e.g., to provide user feedback regarding user input and/or the performance of the desired function. Illumination of light source 174 and/or vibrations and/or audible notifications may be executed in any number of patterns, frequencies, durations, sequences, combinations, colors, brightness levels, etc. to indicate particular information, such as particular input received and/or particular functions or operations enabled and/or initiated, to the pump user or caregiver. FIG. 2C depicts another embodiment of a pump 102 that includes two indicator lights 174.

Figure 3:
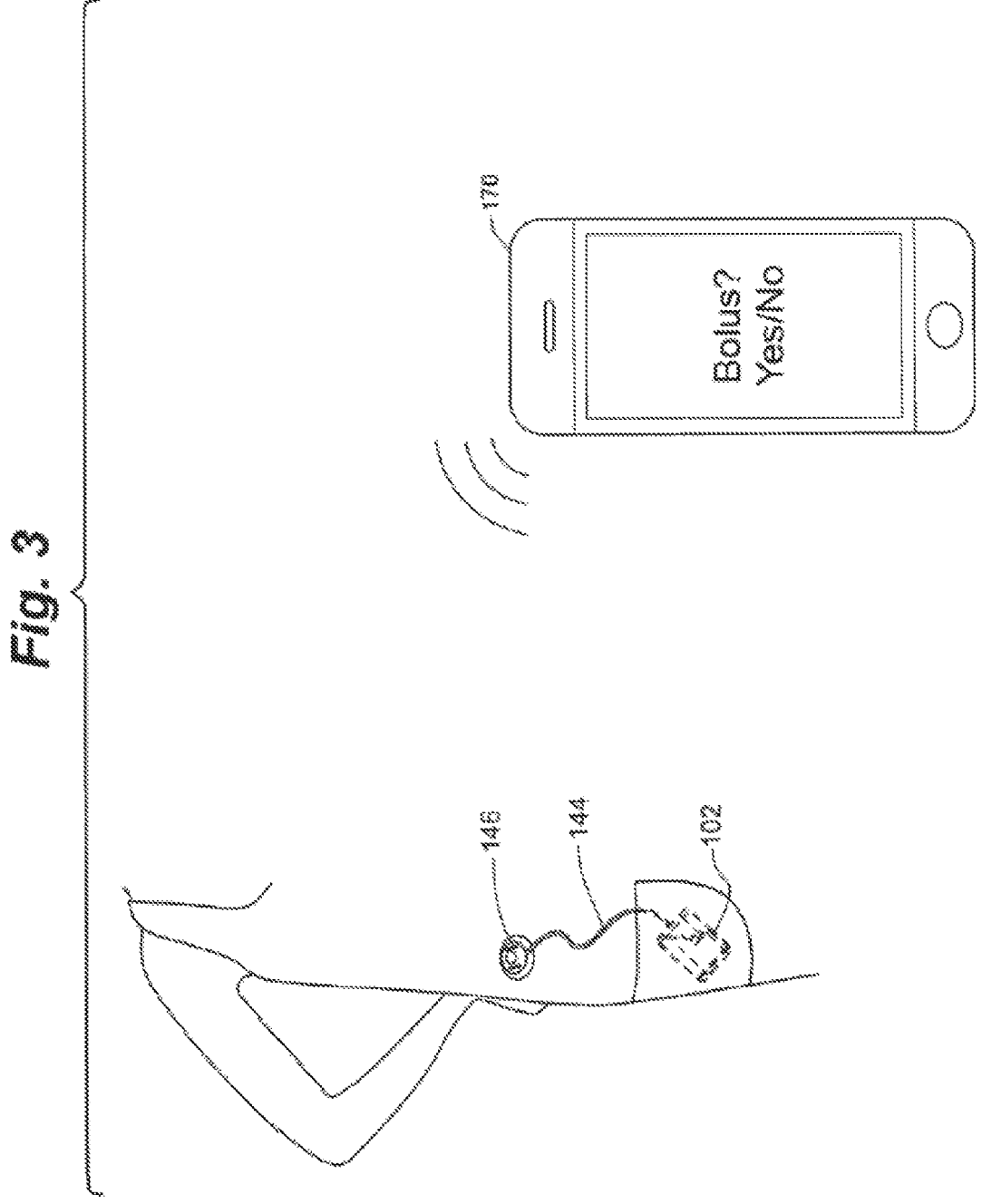
FIG. 3 depicts an embodiment of a pump system according to the disclosure.
Figure 4B:
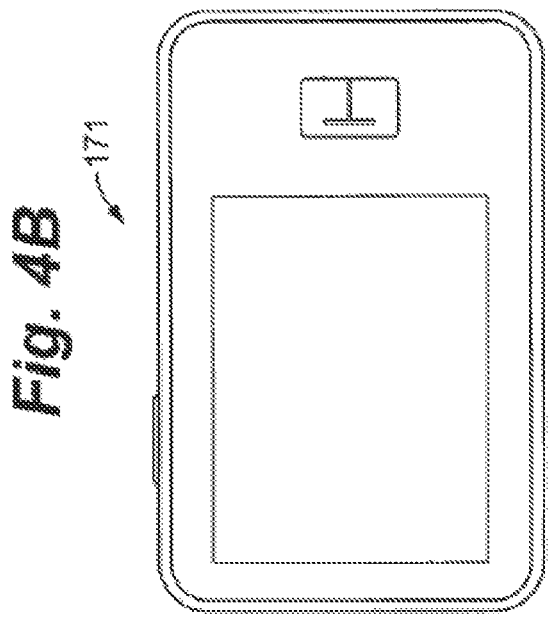
FIGS. 4A-4B depict remote control devices for a pump system according to embodiments of the disclosure.
Figure 4A:
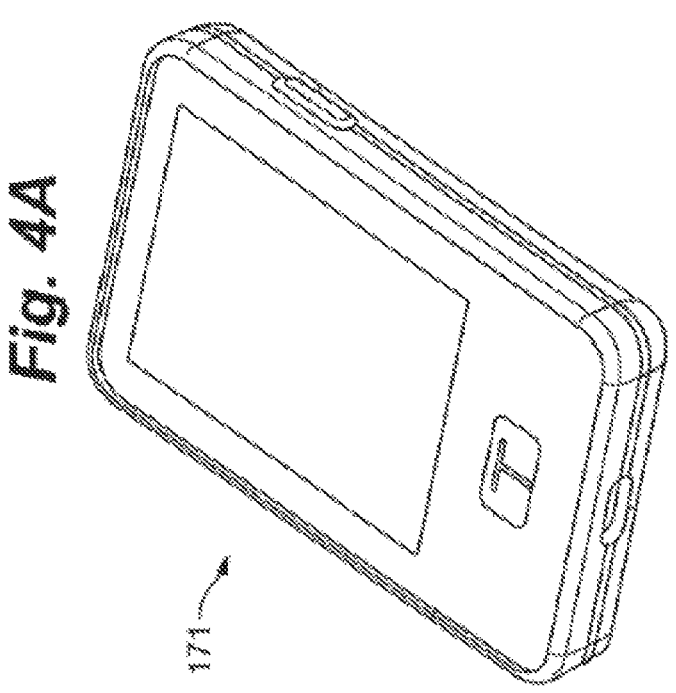

Referring to FIGS. 3-4B, one or more remote control devices 170, 171 can be used to communicate with the processor of pump 102 to control delivery of medicament and transfer data with pump 102 via a wired or a wireless electromagnetic signal, such as via, e.g., a nearfield communication (NFC) radio frequency (RF) modality or other RF modalities such as Bluetooth®, Bluetooth® low energy, mobile or Wi-Fi communication protocols, for example, according to embodiments of the present disclosure. Such a remote control can include, for example, a mobile communication device 170, such as a smart phone (as depicted in FIG. 3) executing a software application for control of the pump, a dedicated remote controller 171 (as depicted in FIGS. 4A-4B), a wearable electronic watch or electronic health or fitness monitor or personal digital assistant (PDA), etc., or a tablet, laptop or personal computer. Such communications between (and among) the one or more remote control devices 170, 171 and pump 102 may be one-way or two-way for, e.g., effective transfer of data among the devices and the pump, control of pump operations, updating software on the devices and/or pump, and allowing pump-related data to be viewed on the devices and/or pump.

Embodiments of the present invention include components capable of and methods using wired and wireless transmission and receipt of signals for exchange of information and commands between and among any of the components as described herein, including, e.g., between a pump and a smartphone; among a pump, a CGM and a smartphone; between a dedicated remote controller and a pump; among a dedicated remote controller, a CGM and a pump; among a dedicated remote controller, a BGM and a pump, and other combinations as would be contemplated by those of skill in the art.

Figures 5A, 5B, 5C, 5D:
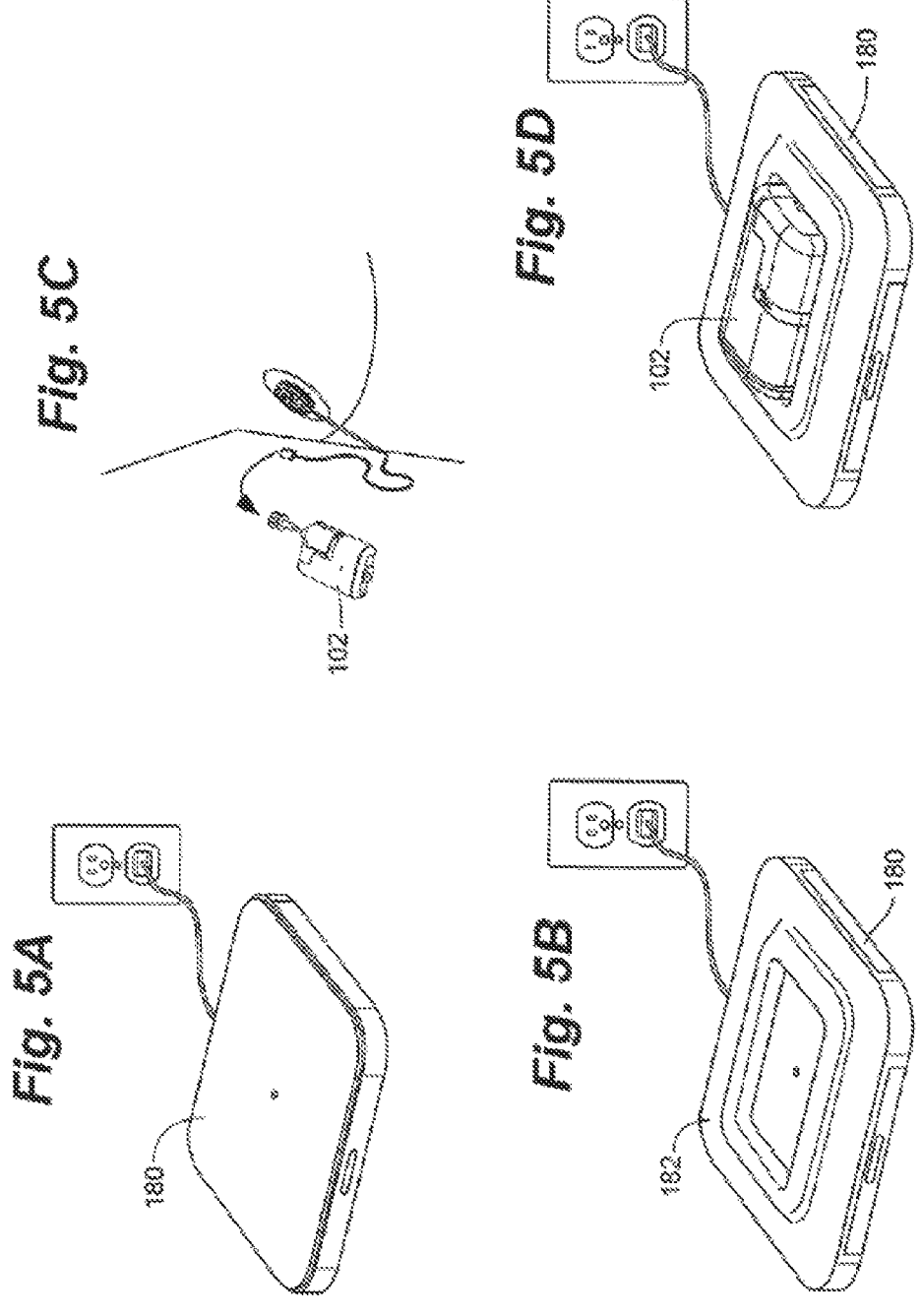
FIGS. 5A-5D depict a procedure for inductively charging a battery of a pump system according to an embodiment of the disclosure.

Referring to FIGS. 5A-5D, pumps according to embodiments of the present disclosure can include one or more rechargeable batteries in and/or associated with the pump drive unit 118. In some embodiments, are chargeable battery can be wirelessly charged, for example through inductive charging by an inductive charging pad 180. As depicted in FIG. 5B, in some embodiments, the charging pad 180 can include a cover 182 having a cutout sized to receive pump 102 in order to properly position and retain pump 102 on the charging pad 180 during recharging. In some embodiments, as shown in FIGS. 5A, 5B and 5D, the charging pad 180 may receive power by being connected to a wall outlet. In other embodiments, the charging pad 180 may additionally or alternatively include a wired and/or wireless power connection to, for example, a computer (e.g., via USB or IEEE 1394), a 12 volt automobile outlet, a battery pack (e.g., via USB or IEEE 1394), optical means, and/or a solar panel, among others.

For a pump 102 to be able to be controlled by a remote control device such as a smartphone 170 operating a software application for controlling the pump or dedicated remote controller 171 via wireless communication such as, for example, Bluetooth, the pump must be paired with the control device to establish the mutual connection between the devices. However, due to the limited communication capabilities of some user-wearable infusion pumps 102 such as those depicted in FIGS. 1A-1C and 2A-2C that do not include a display screen, it may be difficult to cause the pump to participate in the pairing process and to follow the status of the pump during pairing. Embodiments of the present invention therefore employ additional elements of the system to aid in the pairing process.

Figure 6:
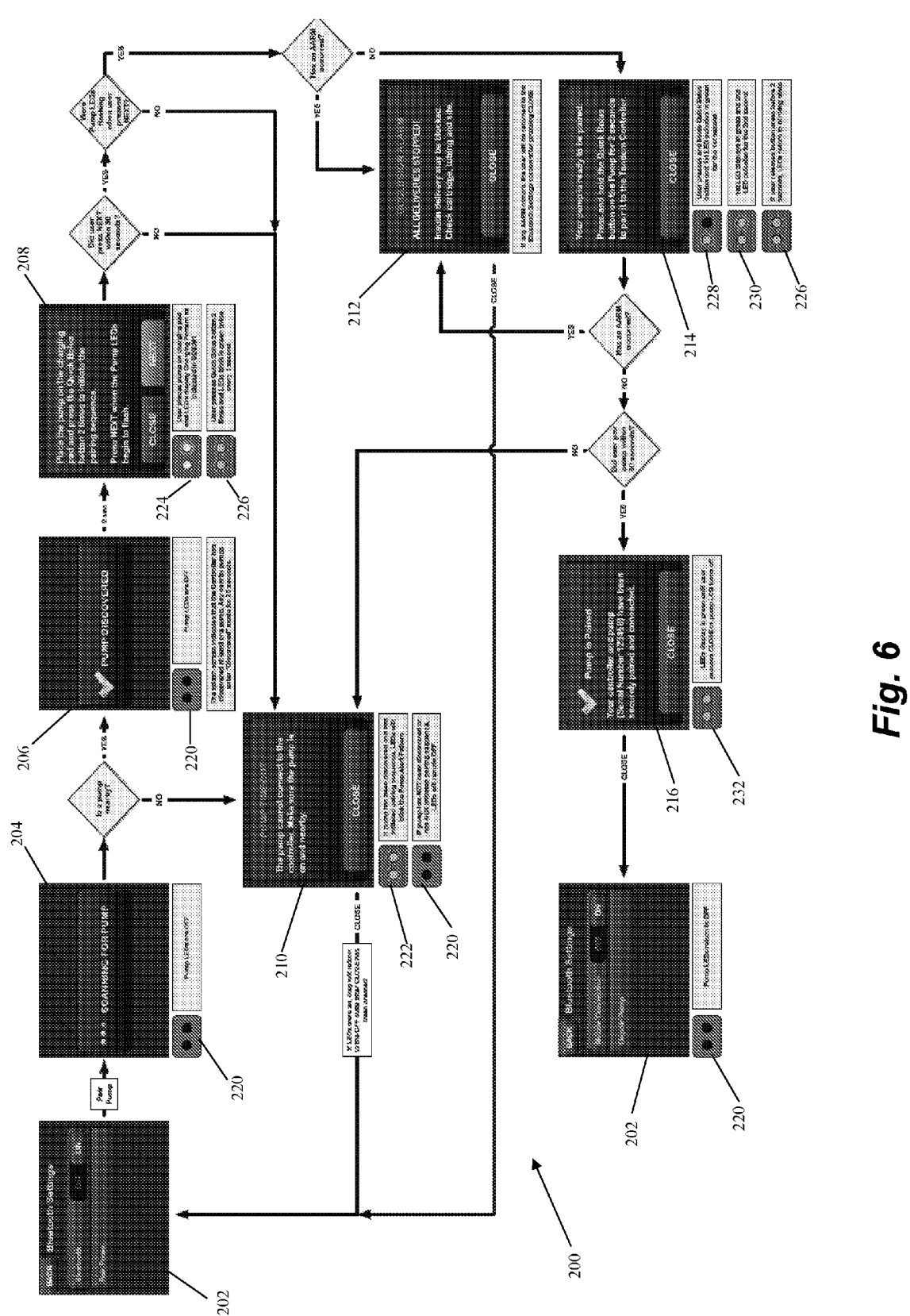
FIG. 6 schematically depicts a pairing sequence for an infusion pump and a remote control device according to an embodiment of the disclosure.
Figure 7I:
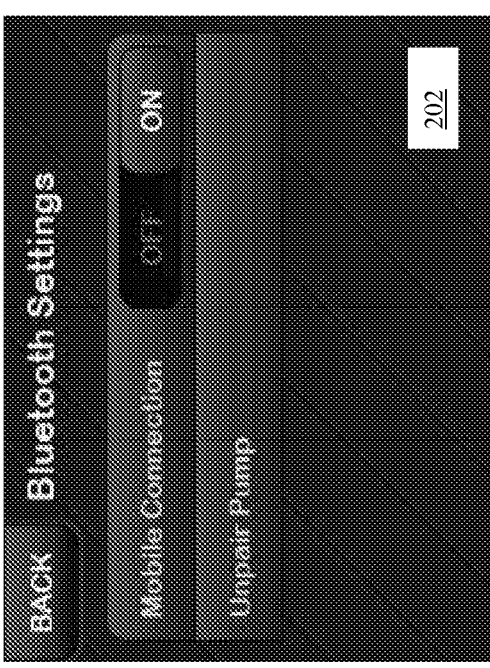

FIG. 6 schematically depicts a pairing sequence 200 for pairing remote control device 170, 171 with an infusion pump 102 according to an embodiment. The display screens 202-216 depicted in FIG. 6 can be displayed on the remote control device 170, 171 whereas the depicted LED annunciation patterns 220-232 depict the indicator lights 174 of a pump 102 such as that depicted in FIG. 2C during the pairing sequence. Display screens 202-216 are further depicted clearly in FIGS. 7A-7I. In some embodiments, a quick bolus, i.e., a bolus delivered using only the button on the pump, is disabled throughout the pairing process due to the need to use the button to initiate the pairing sequence.

A user first navigates to a Bluetooth Settings screen 202 on the remote device 170, 171 and, if not already done so, the device's Bluetooth (or other wireless modality) must be turned on. The pairing process is then initiated by selection of a Pair Pump menu item displayed on the Bluetooth settings screen 202 when the device is not paired to a pump. The remote device 170, 171 then scans for the pump 102 as indicated by a Scanning for Pump screen 204. As the remote device scans for the pump 102, the pump indicator lights 174 are off as indicated by lights 220. If a pump 102 is discovered by the remote device 170, 171, a Pump Discovered screen 206 will be displayed. Once a pump has been discovered, the pump indicator lights 174 will transition from an off state 220 to a discovered state 222. In one embodiment, both indicator lights 172 will blink off and on in a particular color, such as, for example, orange to indicate a pump alert that the pump has been discovered. If a pump is not discovered by the remote device 170, 171, the remote can display a Pump Timeout screen 210 informing the user that the pump and controller could not be connected.

In various embodiments, the pairing sequence can utilize the inductive charging pad 180 (or other charging device) to aid in the pairing process. After the remote device 170, 171 has indicated to the user that a pump 102 is discovered, the remote device 102 can display an initiate pairing screen 208 instructing the user to place the pump 102 on the charging pad 180 and press the pump's input button 172 to initiate the pairing sequence. In one embodiment, the user may be instructed to press the input button 172 twice in succession to initiate the sequence. When the pump 102 is first placed on the charging pad 180, the indicator lights 174 can indicate a charging state 224. After the user has initiated the pairing sequence, the indicator lights 174 can indicate a pairing state 226 such as, for example, continually blinking in a given color (e.g., green). The initiate pairing screen 208 can further instruct the user to press a Next input item once the indicator lights 174 are flashing to indicate that pairing has been initiated. If the user does not press the Next input item within a predetermined period of time after pairing has been initiated, such as, for example, 30 seconds, or if the user presses the Next key when the indicator lights were not in the pairing state 226 (i.e., pairing had not been initiated), the remote 170, 171 display will revert to the Pump Timeout screen 210. See U.S. Patent Publication No. 2018/0193555, previously incorporated by reference herein in its entirety, for further description of how a pump can be configured such that the button 172 can perform different functions in the presence of absence of an inductive charging signal.

If a pump alarm, alert, etc. occurs during the pairing process, such as, for example, an occlusion indicated by the Occlusion Alarm screen 212, the user is instructed to close the alert and is then automatically routed back to the initial Bluetooth Settings screen 202 to reinitiate the pairing process once the cause of the alarm, alert, etc. has been addressed.

If no alarm, alert, etc. has occurred, after the user has pressed the Next input item on the initiate pairing screen 208, a ready to pair screen 214 is displayed on the remote device 170, 171. The ready to pair screen 214 informs the user that the pump is ready to be paired and instructs the user to hold the input button 172 for a given period of time, e.g., two seconds, to pair the pump 102 to the control device 170, 171. The indicator lights 174 can provide visual feedback that the user is properly holding the input button 172 to execute the pairing process. In one embodiment, a first pairing indicator 228 includes a first indicator light pulsating in a given color (e.g., green) during a first portion of the period of time (e.g., the initial second) and then a second pairing indicator 230 includes the first light being stably displayed in the color and the second light pulsating during the second portion of the period of time (e.g., the final second). If the user releases the input button prior to the period of time required for pairing, the indicator lights will revert to the blinking state 226 indicating the device is ready to pair. As noted above, if a pump alarm, alert, etc. occurs during the pairing process, the remote device displays the corresponding alarm or alert screen, such as the Occlusion Alarm screen 212, which will cause the user to be routed back to the initial Bluetooth Settings screen 202 to reinitiate the pairing process once the screen is closed. Similarly, if the user does not pair the pump as instructed on the ready to pair screen 214 within a preset period of time, such as 30 seconds, the Pump Timeout screen 210 will be displayed as discussed above.

If the user has properly paired the pump 102 with the remote device 170, 171, a Pump is Paired screen 216 is displayed confirming to the user that the devices are securely paired and connected. The pairing indicator 232 can display both indicator lights 174 in the solid color to indicate successful pairing on the pump. The Pump is Paired screen 216 instructs the user to close the screen, which returns the remote control 170, 171 display to the Bluetooth Settings screen 202 and the indicator lights 174 to the off state 220. The Bluetooth Settings screen 202 now indicates that the pump is paired and provides an ability to disconnect the pump and the remote device with an Unpair Pump input item.

As noted above, illumination of the one or more indicator lights 174, and particularly in a pump such as that in FIG. 2C having two indicator lights 174, can be executed in any number of patterns, frequencies, durations, sequences, combinations, colors, brightness levels, etc. to indicate particular information. The examples given above with respect to various colors, illumination patterns and combinations, etc. are illustrative only and it should be understood that different information can be conveyed by varying the output of indicator lights 174 in any number of ways.

Figure 8:
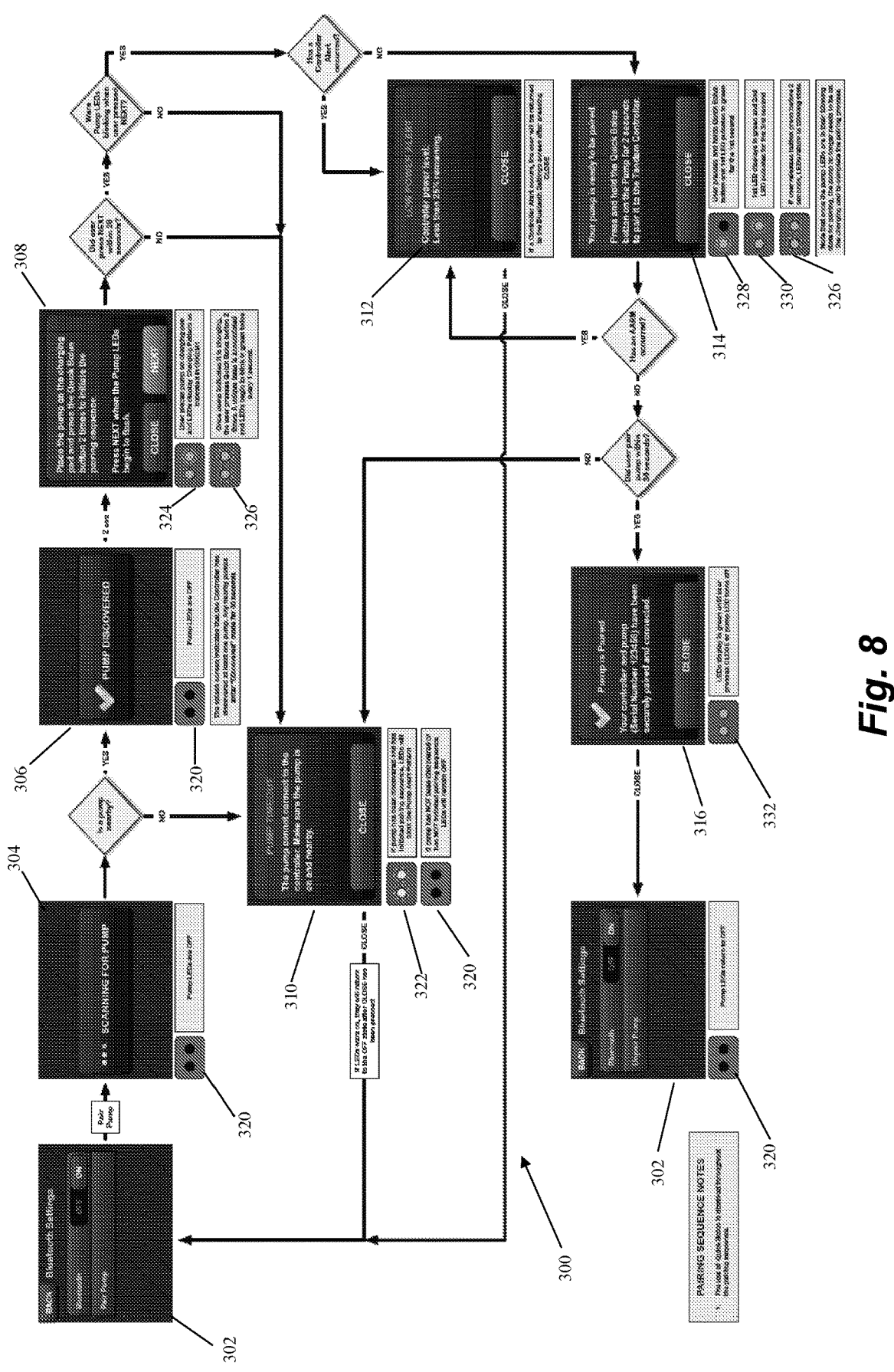
FIG. 8 schematically depicts a pairing sequence for an infusion pump and a remote control device according to an embodiment of the disclosure.
Figure 9:
FIG. 9 depicts an exemplary screen shot on a remote control device for the pairing sequences of FIGS. 6, 8 and/or 10.

FIG. 8 schematically depicts a pairing sequence 300 for pairing a remote control device 170, 171 with an infusion pump 102 according to another embodiment. Sequence 300 is substantially similar to sequence 200 described above. Display screens 302-310 and 314-316 are substantially identical to the corresponding screens in sequence 200 and the transitions between screens substantially similar. As shown in sequence 300, alternatively or in addition to the Occlusion Alarm screen 212 indicating that any pump alarm, alert, etc. during the pairing process can cause the pairing process to terminate, any controller alert, such as that indicated by the controller Low Power Alert screen 312 can also terminate the pairing process. The Low Power Alert screen 312 is shown in greater detail in FIG. 9. Indicator statuses 320-332 of indicator lights 174 are substantially similar to the corresponding indicator statuses 220-232, although, as noted above, the colors, patterns, etc. may be varied. In addition, indicator status 326 notes that, in some embodiments, the pump may also emit a unique sound along with the indicator light pattern to indicate that the pairing sequence has been initiated. Sequence 300 further notes that, in some embodiments, once the pump is in the pairing state as indicated by the pairing state 326 of the indicator lights, the pump no longer needs to be on the charging pad to complete the pairing process. Thus, in some embodiments, the charging pad is only used to initiate the pairing process and does not need to be present to actually pair the pump and the control once the pump is ready to be paired.

Figure 10:
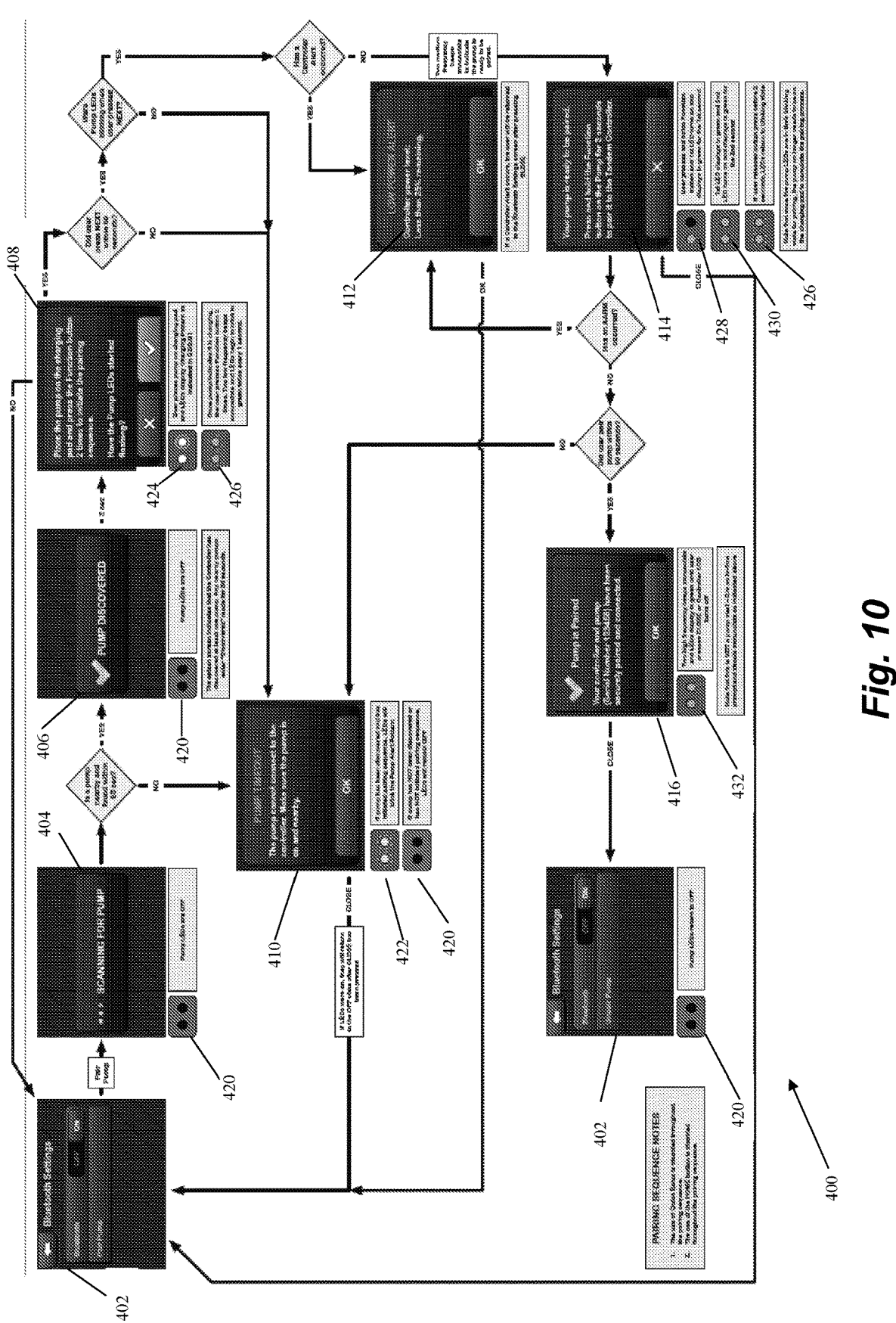
FIG. 10 schematically depicts a pairing sequence for an infusion pump and a remote control device according to an embodiment of the disclosure.
Figure 11B:
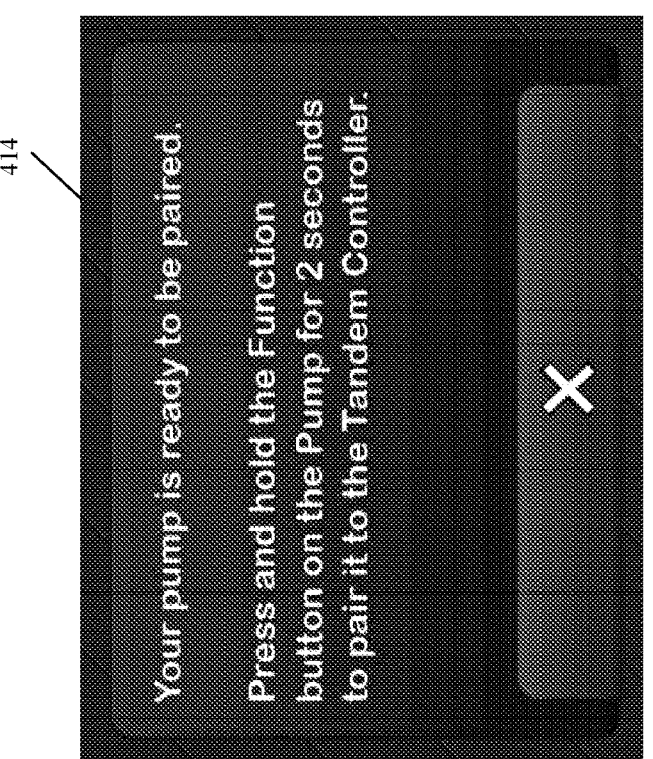
FIGS. 11A-11B depict exemplary screen shots on a remote control device for the pairing sequences of FIGS. 6, 8 and/or 10.
Figure 11A:
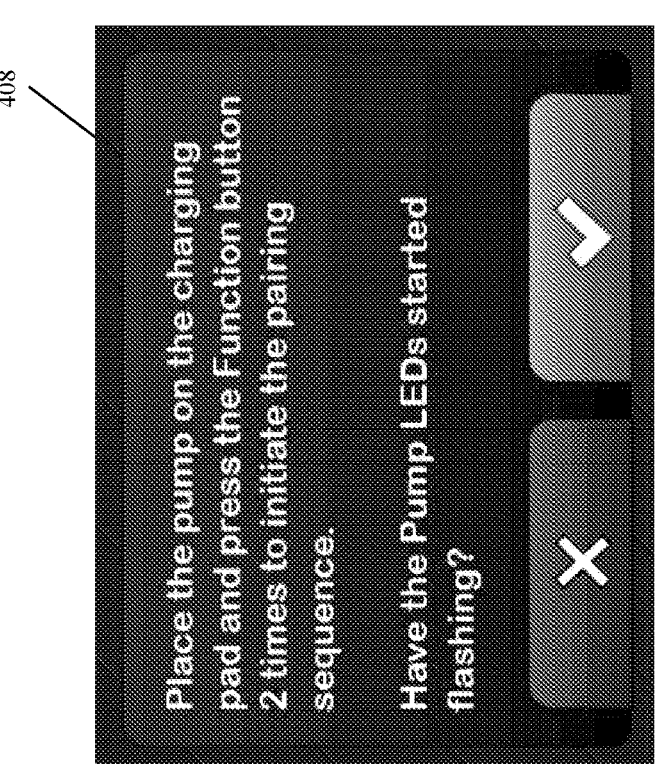

FIG. 10 schematically depicts a pairing sequence 400 for pairing a remote control device 170, 171 with an infusion pump 102 according to another embodiment. Sequence 400 is substantially similar to sequences 200 and 300 described above. Display screens 402-406, 410 and 416 are substantially identical to the corresponding screens in sequences 200 and 300 and screen 412 is substantially identical to the corresponding screen in sequence 300 with the transitions between screens also substantially similar. Screens 408 and 414 are similar to the corresponding screens, but, as shown in FIGS. 11A-11B, including visual X and check mark cues for closing or advancing the screen rather than text. Sequence 400 additionally expressly depicts that if the X icon on screen 408 indicating that the pump indicator lights have not started flashing or the X icon on screen 414 are selected, that the workflow returns to the initial Bluetooth Settings screen 402. Indicator statuses 420-432 of indicator lights 174 are substantially similar to the corresponding indicator statuses 220-232 and 320-332 although, as noted above, the colors, patterns, etc. may be varied. Pairing sequence 400 further notes that a HOME button that may be provided on the remote control to return the remote control display to a home screen or main menu may be disabled during the pairing process such that the pairing process may only be exited from within a screen in the workflow sequence.

Although the pump system described herein is described as a user-wearable pump system that has no display or user interface and is primarily controlled by a remote device, it should be understood that aspects of the present disclosure can be incorporated into other types of infusion pumps. For example, full-featured user-wearable infusion pumps having display and input capabilities, such as a touchscreen display on the pump housing, one example of which is disclosed in U.S. Pat. No. 8,287,495, which is hereby incorporated by reference herein, can incorporate aspects of the present disclosure.

Although the embodiments herein have been specifically described with respect to an ambulatory infusion pump, the inventions disclosed herein could be employed with any other type of programmable medical device capable of receiving and executing remote commands. Such devices include, for example, implantable pumps, defibrillators, spinal cord stimulation systems, etc. Embodiments could further include non-medical applications.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,378,333; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106 and 10,279,107; commonly owned U.S. Patent Publication Nos. 2009/0287180; 2012/0123230; 2013/0053816; 2014/ 0276419; 2014/0276423; 2014/0276569; 2014/0276570; 2016/0082188; 2017/0142658; 2017/0182248; 2017/ 0250971; 2018/0021514; 2018/0071454 and 2018/0193555; commonly owned U.S. patent application Ser. Nos. 16/266, 471; 16/380,475; and Ser. No. 16/423,675.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

The invention claimed is:

1. A system for pairing a user-wearable infusion pump with a remote control device, comprising:
   the user-wearable infusion pump configured to be controlled by the remote control device; and
   the remote control device including a processor configured to present instructions on a display screen for a pairing procedure for pairing the remote control device for control of the user-wearable infusion pump, wherein:
      feedback is provided during the pairing procedure as to indicate an ongoing status of the pairing procedure for pairing the remote control device with the user-wearable infusion pump, and
      successful pairing of the remote control device with the user-wearable infusion pump is confirmed via both the display screen and the user-wearable infusion pump.

2. The system of claim 1, wherein the user-wearable infusion pump includes one or more indicator lights and wherein at least one of providing feedback with the user-wearable infusion pump and confirming successful pairing with the user-wearable infusion pump is provided by the one or more indicator lights.

3. The system of claim 1, wherein at least one of providing feedback with the user-wearable infusion pump and confirming successful pairing with the user-wearable infusion pump is provided audibly by the user-wearable infusion pump.

4. The system of claim 1, wherein at least one of providing feedback with the user-wearable infusion pump and confirming successful pairing with the user-wearable infusion pump is provided with one or more vibrations of the user-wearable infusion pump.

5. The system of claim 1, wherein the processor is configured to presenting an instruction on the display screen for the user-wearable infusion pump to be placed on an inductive charging device.

6. The system of claim 5, wherein the pairing procedure is only initiated after it is determined that the user-wearable infusion pump has been placed on the inductive charging device.

7. The system of claim 6, where the pairing procedure continues if the user-wearable infusion pump is removed from the inductive charging device after the pairing procedure is initiated.

8. The system of claim 1, wherein the pairing procedure is not initiated until a pairing initiation input is detected from the user-wearable infusion pump.

9. The system of claim 8, wherein the pairing initiation input is input at the user-wearable infusion pump with an input button disposed on the pump.

10. The system of claim 1, wherein the processor is configured to present one or more instructions on the display screen for a user to interact with an input button of the user-wearable infusion pump.

11. The system of claim 1, the processor is configured to detect a pump alarm or alert prior to confirm successful pairing and terminate the pairing procedure in response to detecting the pump alarm or alert.

12. A system for pairing a user-wearable infusion pump with a remote control device, comprising:
   the user-wearable infusion pump configured to be controlled by the remote control device; and the remote control device configured to control the user-wearable infusion pump, the remote control device including a processor configured to:

present an instruction on a display screen for the user-wearable infusion pump to be placed on an inductive charging device;

determine whether the user-wearable infusion pump has been placed on the inductive charging device; and initiate a pairing procedure for pairing the user-wearable infusion pump with the remote control device responsive to determining that the user-wearable infusion pump has been placed on the inductive charging device.

13. The system of claim 12, wherein the pairing procedure continues if the user-wearable infusion pump is removed from the inductive charging device after the pairing procedure is initiated.

14. The system of claim 12, wherein the pairing procedure is terminated if the user-wearable infusion pump is removed from the inductive charging device after the pairing procedure is initiated.

15. The system of claim 12, wherein feedback is provided during the pairing procedure as to indicate an ongoing status of the pairing procedure for pairing the remote control device with the user-wearable infusion pump.

16. The system of claim 12, wherein the processor is further configured to, responsive to determining that the user-wearable infusion pump has been placed on the inductive charging device but prior to initiating the pairing procedure, determine that the user-wearable infusion pump is available for the pairing procedure based on a user input received at the user-wearable infusion pump.

17. A device for controlling a user-wearable infusion pump, comprising:

a processor configured to:

present instructions on a display screen for a pairing procedure for pairing a remote control device for control of the user-wearable infusion pump;

provide feedback during the pairing procedure as to indicate an ongoing status of the pairing procedure for pairing the remote control device with the user-wearable infusion pump; and confirm successful pairing of the remote control device with the user-wearable infusion pump via the display screen, wherein the successful pairing is also confirmed via an output provided by the user-wearable infusion pump.

18. The device of claim 17, wherein the processor is configured to presenting an instruction on the display screen for the user-wearable infusion pump to be placed on an inductive charging device.

19. The device of claim 18, wherein the pairing procedure is only initiated after it is determined that the user-wearable infusion pump has been placed on the inductive charging device.

20. The device of claim 19, where the pairing procedure continues if the user-wearable infusion pump is removed from the inductive charging device after the pairing procedure is initiated.

* * * * *